United States Patent [19]
Avellanet

[11] Patent Number: 6,036,725
[45] Date of Patent: Mar. 14, 2000

[54] EXPANDABLE ENDOVASCULAR SUPPORT DEVICE

[75] Inventor: Francisco J. Avellanet, Coral Gables, Fla.

[73] Assignee: General Science and Technology, Miami, Fla.

[21] Appl. No.: 09/095,249

[22] Filed: Jun. 10, 1998

[51] Int. Cl.[7] .................................................. A61F 2/06
[52] U.S. Cl. ................................................................ 623/1
[58] Field of Search .......................................... 623/1, 12

[56] References Cited

U.S. PATENT DOCUMENTS

| | | |
|---|---|---|
| 3,304,557 | 2/1967 | Polansky . |
| 3,730,835 | 5/1973 | Leeper et al. . |
| 3,868,956 | 3/1975 | Alfidi . |
| 4,106,129 | 8/1978 | Carpentier et al. . |
| 5,019,090 | 5/1991 | Pinchuk . |
| 5,123,917 | 6/1992 | Lee . |
| 5,190,546 | 3/1993 | Jervis . |
| 5,217,483 | 6/1993 | Tower . |
| 5,282,824 | 2/1994 | Gianturco . |
| 5,292,331 | 3/1994 | Boneau . |
| 5,443,496 | 8/1995 | Schwartz et al. . |
| 5,549,635 | 8/1996 | Solar . |
| 5,562,697 | 10/1996 | Christiansen . |
| 5,562,724 | 10/1996 | Vorwerk et al. . |
| 5,597,378 | 1/1997 | Jervis . |
| 5,665,116 | 9/1997 | Chaisson ...................................... 623/1 |
| 5,674,278 | 10/1997 | Boneau . |
| 5,681,346 | 10/1997 | Orth ............................................ 623/1 |
| 5,693,087 | 12/1997 | Parodi . |
| 5,720,776 | 2/1998 | Chuter et al. . |
| 5,728,152 | 3/1998 | Mirsch et al. . |
| 5,733,328 | 3/1998 | Fordenbacher .............................. 623/1 |
| 5,776,180 | 7/1998 | Goicoechea ................................. 623/1 |
| 5,871,538 | 2/1999 | Dereume ..................................... 623/1 |

FOREIGN PATENT DOCUMENTS

| | | |
|---|---|---|
| 0 312 852 A1 | 6/1988 | European Pat. Off. . |
| 0 587 197 A1 | 11/1991 | European Pat. Off. . |

OTHER PUBLICATIONS

Handbook of Coronary Stents, Second Edition, 1998, edited by Serruys and Kutryk, pp. 77–84.
Handbook of Coronary Stents, Second Edition, 1998, edited by Serruys and Kutryk, pp. 46–53.

*Primary Examiner*—Michael J. Milano
*Attorney, Agent, or Firm*—David P. Gordon; David S. Jacobson; Thomas A. Gallagher

[57] ABSTRACT

A stent includes a cylindrical tubular form and a plurality of foil members coupled about to the exterior of the tubular form. The foil members are spaced apart around the circumference of the tubular form to provide spaces between the segments when the stent is in an expanded state, the spaces permitting the tubular form to be contracted to a small diameter for delivery to an implant site. According to a first embodiment, the stent is self-expanding, and the tubular form is formed from a resilient wire, preferably having a plurality of longitudinal back and forth bends. According to a second embodiment, the stent is self-expanding and comprised of a plurality of tubular portions linked together, each of the portions having a plurality of foil members coupled about the circumference of the portion. According to a third embodiment, the stent is pressure expandable, and the tubular form of the stent is made from a malleable slotted tube or one or more malleable wires. The malleable tubular form has a plurality of foil members coupled about its circumference. In each embodiment, the foil members contact the wall of the blood vessel at a relatively large and flat surface which minimizes trauma at the implant location. In addition, the foil members provide additional strength to the stent.

32 Claims, 7 Drawing Sheets

EXPANDABLE ENDOVASCULAR SUPPORT DEVICE

BACKGROUND OF THE INVENTION

1. Field of the Invention

This invention relates broadly to vascular prostheses. More particularly, this invention relates to coronary stents.

2. State of the Art

Cardiovascular disease, including atherosclerosis, is one of the leading causes of death in the United States. A number of methods have been developed for treating coronary heart disease, and particularly for treating complications resulting from atherosclerosis and other forms of coronary arterial narrowing.

One of the most important recent developments for the treatment of atherosclerosis and other forms of coronary vascular narrowing is percutaneous transluminal coronary angioplasty, hereinafter referred to as "angioplasty". The angioplasty procedure enlarges the lumen of the affected coronary artery by radial hydraulic expansion, and is accomplished by inflating a balloon within the narrowed lumen of the coronary artery. Radial expansion of the coronary artery by the balloon operates to flatten soft plaque, crack and split hardened deposits, and stretch the wall of the artery to a greater diameter.

Angioplasty is typically performed by first introducing a thin-walled hollow guiding catheter into the body via a relatively large arterial vessel, such as the femoral artery in the groin area. The guiding catheter is advanced through the femoral artery, into the iliac artery, into the ascending aorta, negotiated through the sharp turn of the aortic arch, and descended into the aortic cusp. Once at the aortic cusp, the guiding catheter may be moved to either of the left or right coronary arteries.

After the guiding catheter is advanced to the ostium of the coronary artery to be treated by angioplasty, a flexible guidewire is inserted through the guiding catheter to the location to be treated and extended through the area of constriction. A balloon catheter is then advanced over the guidewire and inflated at the locus of the constriction.

Unfortunately, while the affected artery can be enlarged, in some instances the vessel restenoses chronically, or closed down acutely, negating the positive effect of the angioplasty procedure. In the past, such restenosis has required the angioplasty procedure to be repeated or necessitated open heart surgery. While restenosis does not occur in the majority of cases, it occurs frequently enough such that such complications comprise a significant percentage of the overall failures of the angioplasty procedure, for example twenty-five to forty percent of such failures.

To lessen the risk of restenosis, stents have been used across the vascular lesion to mechanically maintain a previously balloon-expanded blood vessel in a dilated condition. In general, a stent is advanced to the site of the lesion in a constricted diameter state, and then expanded in the lesion to keep the vascular passageway open. Effectively, the stent overcomes the natural tendency of the vessel walls of some patients to close back down, thereby maintaining a more normal flow of blood through the blood vessel than otherwise possible.

Various types of stents have been used, generally falling into two categories: pressure-expandable and self-expanding. Pressure-expandable stents are typically formed of a malleable material, e.g., stainless steel or tantalum, and are deployed on an inflatable balloon or other expanding member such that upon inflation of the balloon or expansion of the expanding member, the stent will be radially enlarged to a desired diameter such that the stent becomes positioned against the surrounding blood vessel wall. Pressure-expandable stents are disclosed in U.S. Pat. Nos. 5,135,336 to Hulstead; 4,733,685 to Palmaz; 4,922,905 to Strecker; 4,950,227 to Savin et al.; 5,041,126 to Gianturco; 5,108,416 to Ryan et al.; 5,217,483 and 5,161,547 to Tower; and 5,443,496 to 5,443,496 to Schwartz et al. Pressure-expandable stents are generally formed from either a tube of the malleable material which is laser-cut to remove portions of the material to create slots or windows in the tube, i.e., a 'slotted tube', or formed of one or more inelastic malleable wires coupled together in a tubular form by one or more links. Either type of stent permits the stent to be diametrically expansibly deformed under pressure.

Pressure expandable stents of the 'slotted tube' type do provide a relatively large flattened surface area for contact with the inner surface of the vascular wall, resulting in reduced trauma to the lesion. However, the stents are relatively stiff and hard to maneuver through the tortuous curves of the vessel structure. In addition, the stent implant procedure is complicated, requiring the stent to be sufficiently expanded to prevent the stent from inadvertent release from the location of the lesion, yet limited in its expansion so as to not cause additional injury to the vessel wall. Moreover, pressure-expandable stents do not readily conform to the shape of the vessel at the lesion, and may overstretch the vessel wall at one location while insufficiently supporting the wall at another location. Furthermore, 'slotted tube' stents are relatively costly and difficult to manufacture.

Self-expanding stents are generally formed from a spring metal or other resilient material and deployable through a guiding catheter on a delivery catheter covered with a lubricous sleeve. When the sleeve is withdrawn over the self-expanding stent, the stent automatically expands so as to exert pressure against the surrounding blood vessel wall. Self-expanding stents are disclosed in U.S. Pat. Nos. 4,580, 568 to Gianturco; 4,830,003 to Wolff et al.; 5,549,635 to Solar; 5,562,697 to Christiansen; and 5,292,331 and 5,674, 278 to Boneau. Such stents are typically formed from a single small diameter wire having a multiplicity of back and forth bends in a zig-zag or sinusoidal path to form an elongate self-expanding structure, or a plurality of self-expanding segments coupled by links, each of the segments defined by a wire having a zig-zag or sinusoidal path, or a plurality of plaited wires.

Self-expanding stents tend to have great flexibility, primarily due to the materials used and the structures formed, and can be more easily maneuvered through the curves of blood vessels to the lesion site. However, self-expanding wire stents have been less successful in use, in some cases causing injury at the locus of implantation. This may be because the construction of self-expanding wire stents tends to require the use of very narrow wires, and such construction translates to a smaller surface area of the stent available for contact against the blood vessel wall. It is believed that, as a result of the small surface area, the pressure of the wire against the vessel causes injury to the blood vessel wall. In addition, self-expanding stents do not necessarily have the structural rigidity to provide the requisite support of a damaged coronary blood vessel.

SUMMARY OF THE INVENTION

It is therefore an object of the invention to provide a endovascular support device having a relatively large surface area.

It is another object of the invention to provide an endovascular support device which provides substantial structural support.

It is also an object of the invention to provide an endovascular support device which has a high degree of maneuverability.

It is a further object of the invention to provide an endovascular support device which conforms to the shape of lesion.

In accord with these objects, which will be discussed in detail below, a stent is provided comprising a generally cylindrical tubular form and a plurality of foil members coupled about and to the outer periphery of the tubular form. The foil members are spaced apart around a circumference of the outer periphery of the tubular form such that spaces are provided between the foil members when the stent is in an expanded state. The spaces permit the tubular form to be contracted in diameter to a sufficiently small diameter for delivery to a lesion without adjacent segments interfering with each other. In situ, when the tubular form of the stent is expanded, the foil members move radially outward, and provide a relatively large surface for contact with the vessel wall.

According to a first embodiment of the invention, the stent is a self-expanding stent comprised of a resilient wire provided with a plurality of back and forth bends, the wire being curved about in a direction substantially orthogonal to the bends such that the ends of the wire meet and thereby form the wire into a tubular form. The foil members are preferably in the shape of tubular segments. Preferably four to eight foil members are evenly spaced about the circumference of the tubular wire form. The foil members are coupled to the wire preferably by welding in a manner which does not substantially impede the ability of the tubular form to be contracted and to self-expand in diameter.

According to a second embodiment of the invention, substantially similar to the first embodiment, the stent is comprised of a plurality of tubular segments linked together.

According to another embodiment of the invention, similar to the first embodiment, the stent is a pressure-expandable stent comprised of a malleable material provided with a tubular form. The foil members are spaced about the circumference of the outer periphery of the tubular form. The foil members are coupled to the tubular form preferably by welding such that the weld does not substantially impede the ability of the tubular form to be expanded in diameter.

According to any embodiment, the stent may be provided in a range of sizes, preferably from 1 mm to 50 mm. With relatively short stents, the foil members provide additional strength. With relatively long stents, the foil members are preferably relatively narrow (in the direction of the longitudinal axis of the stent) and a plurality of spaced apart foil members may be provided along the length of the stent as well as around the circumference of the stent. The spaces between the foil members along the length of a relatively long stent permit the stent to more easily bend through curved blood vessels.

The self-expanding stent according to the invention may be deployed according to well-known deployment techniques for self-expanding stents. The stent is positioned at the distal end of a catheter with a lubricous sleeve placed over the stent to hold the stent in a contracted state with a relatively small diameter. The stent may then be implanted at the site of a lesion by advancing the catheter over a guidewire to the location of the lesion and then withdrawing the sleeve from over the stent. The stent will automatically expand and exert pressure on the wall of the blood vessel at the site of the lesion. The catheter, sleeve, and guidewire may then be removed from the patient.

The pressure-expandable stent according to the invention may also be deployed according to well-known techniques. The stent is deployed on an inflatable balloon or other expandable member such that upon inflation of the balloon or expansion of the expandable member, the stent will radially expand and be maintained at a desired diameter such that the stent becomes fixedly positioned against the surrounding vessel wall.

With the above embodiments, the stent of the invention has several advantages. First, the foil members which contact the wall of the blood vessel provide both a relatively large surface area which complies to the inner surface of the blood vessel wall. The shape and relative size of the contact surface minimizes trauma to the implant location. Second, the spaced apart relation of the foil members permits a relatively strong stent to be contracted to a size and structure which permits relatively easy advancement and deployment of the stent. Third, particularly with respect to the self-expanding stent, the foil members provide additional strength to the stent. Fourth, with respect to both self-expanding and pressure-expandable stents, the foil members enhance fixation of the stent and further provide structural stability enabling the use of shorter, more maneuverable stents.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
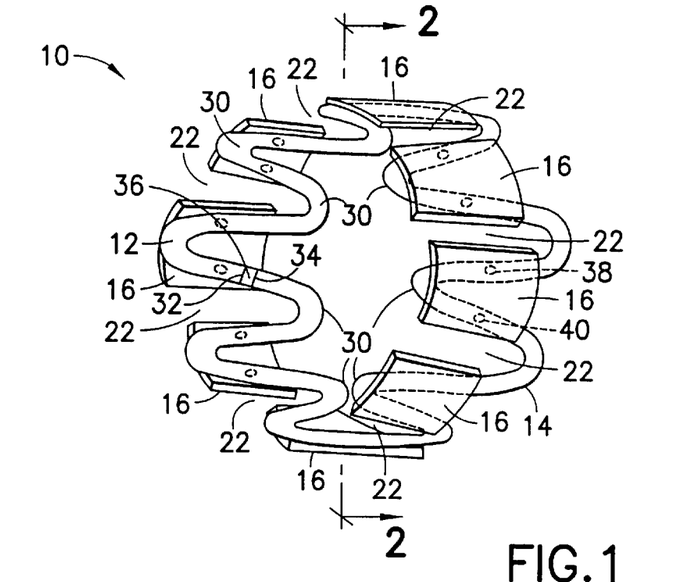
FIG. 1 is a perspective view of a first embodiment of a stent according to the invention, the stent being shown in an expanded position.
Figure 2:
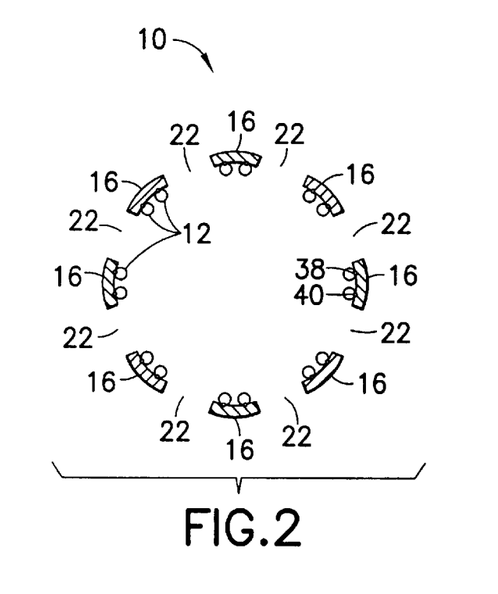
FIG. 2 is a section view across line 2—2 in FIG. 1.
Figure 3:
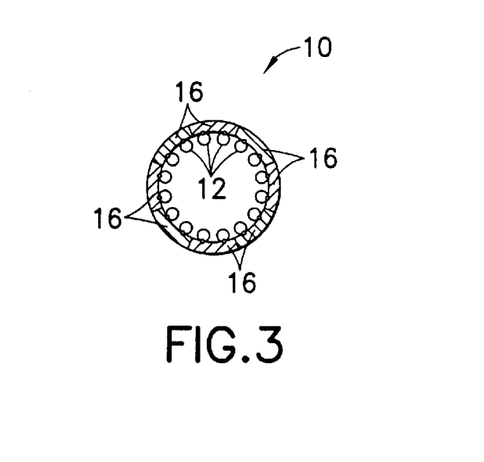
FIG. 3 is a section view of the first embodiment of the stent in a closed position.

Turning now to FIGS. 1 to 3, a first embodiment of a stent 10 according to the invention is shown. The stent 10 includes a metal cylindrical tubular form 14 and a plurality of foil members 16 coupled about and to the exterior of the tubular form. The foil members 16 are spaced apart around the circumference of the tubular form to provide spaces 22 between the segments 16 when the stent is in an expanded state (FIG. 2). The spaces 22 permit the tubular form 14 to be contracted down to the small diameter required for delivery through the blood vessel to the site of the lesion. Accordingly, as described in more detail below, preferably the adjacent segments 16 are arranged so as not to interfere with each other and inhibit diametrical contraction of the stent.

More particularly, and according to a first embodiment of the invention, the stent 10 is designed to be self-expanding. As such, the metal tubular form 14 is formed from a resilient wire 12 having a plurality of longitudinal back and forth bends 30 and further bent into the tubular form in a direction substantially orthogonal to the bends such that the ends 32, 34 of the wire 12 meet. The ends 32, 34 are coupled together, preferably by a weld 36, to maintain the wire 12 in the tubular form 14.

The wire is preferably made from a resilient spring metal such as nitinol or a twisted and drawn wire, e.g., the wires disclosed in co-owned U.S. Ser. No. 09/044,203 filed Mar. 17, 1998, and entitled "Multifilament Nickel Titanium Alloy Drawn Superelastic Wire", co-owned U.S. Ser. No. 09/087, 476, also filed Mar. 17, 1998, and also entitled "Multifilament Nickel Titanium Alloy Drawn Superelastic Wired", and co-owned U.S. Ser. No. 09/060,969, filed Apr. 15, 1998, and entitled "Multifilament Drawn Radiopaque Highly Elastic Cables and Methods of Making the Same", the disclosures of which are hereby incorporated by reference herein in their entireties. The wire 12 has a diameter of preferably approximately 0.002 to 0.009 inches, and more preferably is flattened such that the wire is larger in one cross-sectional dimension, and further such that the flattened portion is provided on the outer periphery of the tubular form 14. The bends 30 of the wire preferably form a sinusoid having an amplitude of preferably approximately 2 mm to 4 mm.

Figure 4:
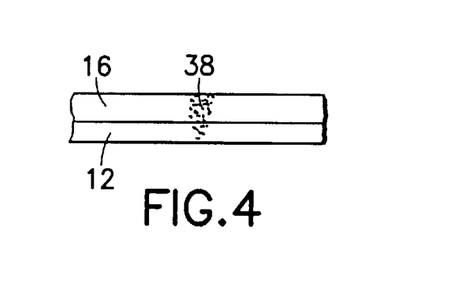
FIG. 4 is a partial section view of the coupling of the wire component of the stent to the foil component of the stent.

The foil members are preferably made from stainless steel, titanium, nickel-titanium alloy, or platinum. The foil members 16 are preferably in the shape of tubular segments, i.e., at least the outer surface of the foil members preferably have a small radial curve. The foil members 16 have a thickness of preferably approximately 0.003 to 0.006 inches. Preferably eight foil members 16 are equally spaced from one another about the tubular form 14 and arranged such that each foil member is positioned substantially tangential to the circumference of the tubular form. Each foil member 16 is coupled to the wire 12 preferably at two locations and preferably by welds 38, 40. The location of the welds 38, 40 is such that the welds do not substantially impede the ability of the stent 10 to expand and be contracted in diameter. Referring to FIG. 4, the welds, e.g., weld 38, are preferably provided between the wire 12 and the foil member by the process of electron beam welding, laser welding, or resistance welding, thereby permitting the weld 38 to be narrowly focused at the desired location.

The stent preferably has a length anywhere in the range from approximately 1 mm to 50 mm, and a compressed to expanded diameter ratio of approximately one to four and a half. Examples of expanded diameters include preferably approximately 2 mm to 9 mm for coronary stents, 6 mm to 10 mm for carotid stents, 6 mm to 10 mm for femoral stents, and 8 mm to 12 mm for iliac stents.

Figure 5:
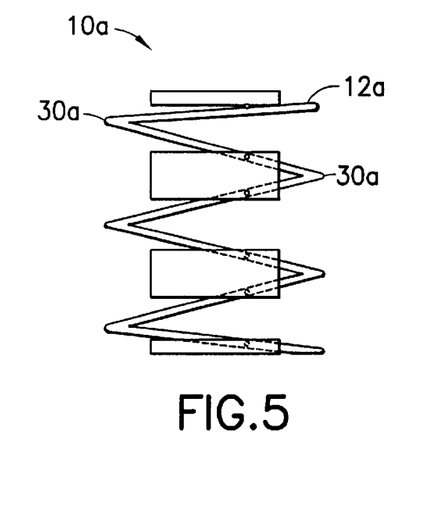
FIG. 5 is a side view of a first alternate arrangement of the wire of the first embodiment of the stent invention.
Figure 6:
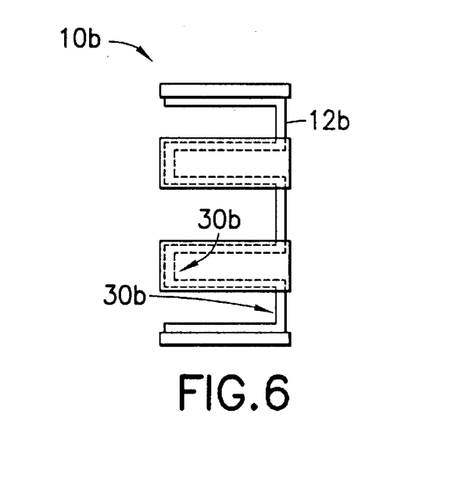
FIG. 6 is a side view of a second alternate arrangement of the wire of the first embodiment of the stent of the invention.

It will be appreciated that the wire 12 of the stent 10 may be provided in a shape other than sinusoidal. Turning to FIG. 5, the wire 12a of the stent 10a may be provided in a zig-zag shape with relatively sharp bends 30a. Referring to FIG. 6, the wire 12b of the stent 10b may also be provided in a squared shape, with substantially ninety degree bends 30b.

Figure 7:
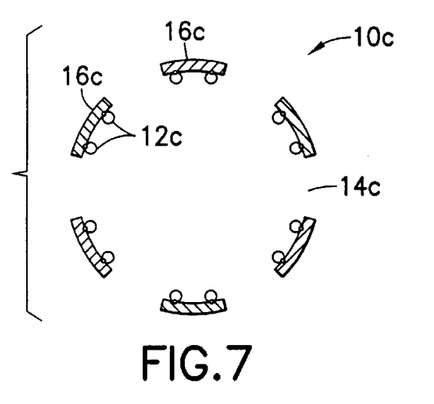
FIG. 7 is a front section view of a first alternate number of foil members for the first embodiment of the stent of the invention.
Figure 8:
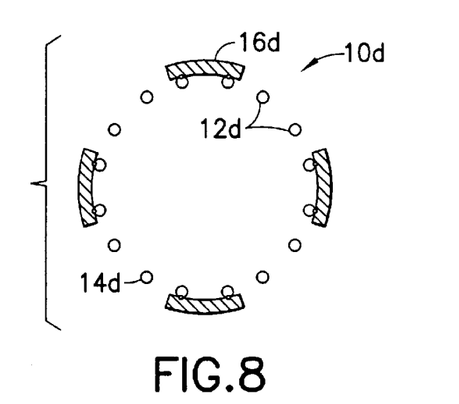
FIG. 8 is a front section view of a second alternate number of foil members for the first embodiment of the stent of the invention.

The stent 10 may also be provided with other than eight foil members 16. Turning now to FIG. 7, six foil members 16c, preferably at sixty degrees of separation, may be coupled about the tubular form 14c of the stent 10c. Moreover, referring to FIG. 8, four foil members 16d may also be provided about the tubular form 14d, preferably at approximately ninety degrees of separation from each other. As shown in FIG. 8, it will be appreciated that foil members 16d need not be located at all locations which may contact a blood vessel wall when the stent is deployed and expanded at an implant site; i.e., some outer peripheral locations of the wire 12d may be bare of foil members 16d.

Figure 9:
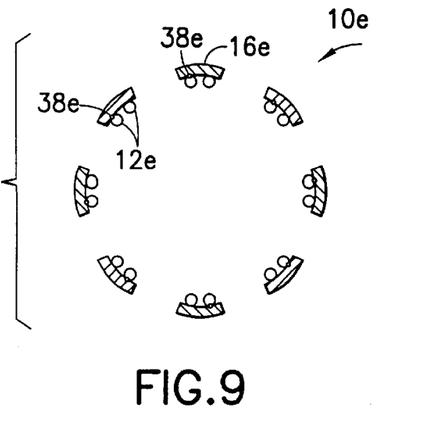
FIG. 9 is a front section view of a first alternate arrangement of the foil members about the tubular form of the first embodiment of the stent of the invention, the stent shown in an expanded position.
Figure 10:
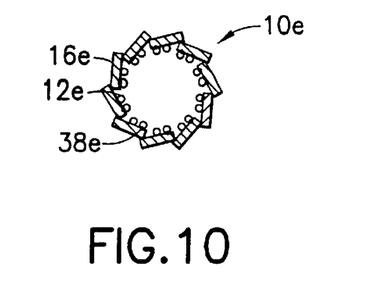
FIG. 10 is a view similar to FIG. 9 with the stent shown in a contracted position.

Turning now to FIGS. 9 and 10, an alternative arrangement of the foil members 16e about the tubular form 14e of the stent 10e is shown. The foil members 16e are arranged such that when the stent 10e is diametrically contracted a portion of each foil member preferably overlaps a portion of another adjacent foil member, thereby permitting contraction to a relatively smaller diameter, or the use of relatively larger foil members and contraction to substantially the same diameter as described above with respect to stent 10. In order to effect the overlapping arrangement of the foil members 16e, each foil member 16e is coupled to the wire 12e, preferably by a weld 38e, preferably at only one location.

Figure 11:
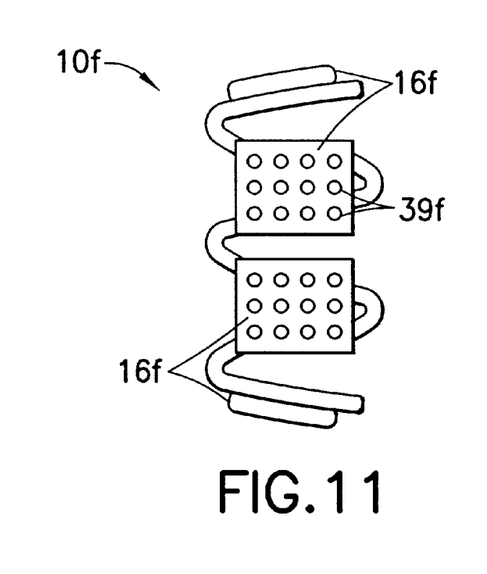
FIG. 11 is a side view of a stent according to a first embodiment of the invention, showing a first alternate construct of the foil members of the stent.
Figure 12:
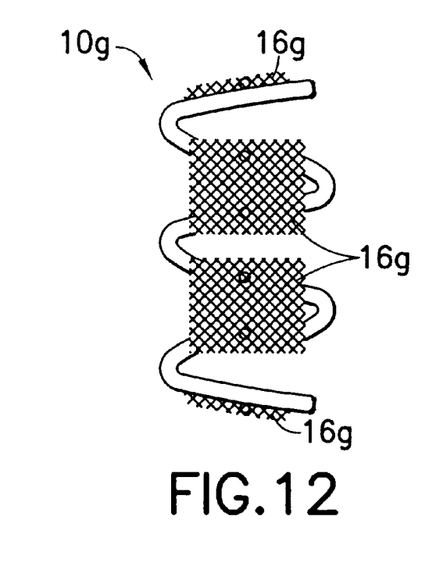
FIG. 12 is a side view of a stent according to a first embodiment of the invention, showing a second alternate construct of the foil members of the stent.

Turning now to FIG. 11, the foil members 16f of the stent 10f may also be perforate having a plurality of holes 39f. Referring to FIG. 12, as another alternative, the foil members 16g of the stent 10g may be formed from a wire mesh. Moreover, with the substantially solid foil, perforate foil, or mesh foil, the foil may be coated or impregnated with a thin layer of PTFE, e.g., 0.0001 to 0.002 inches of PTFE; a thermoplastic elastomer, e.g., nylon, silicone, polyurethane, polypropylene, or polyamide; and/or heparin. The coating or impregnation provide advantages of diminished platelet aggregation, reduced thrombosis, and allows re-endothiliazation of the stent 'surface'.

Figure 13:
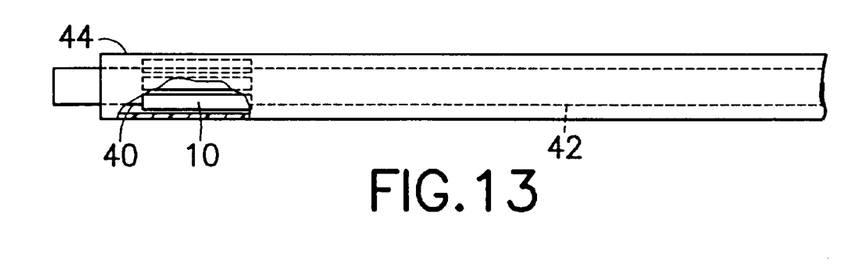
FIG. 13 is a partial section view of the stent according to the first embodiment of the invention positioned at the distal end of a deployment instrument.
Figure 14:
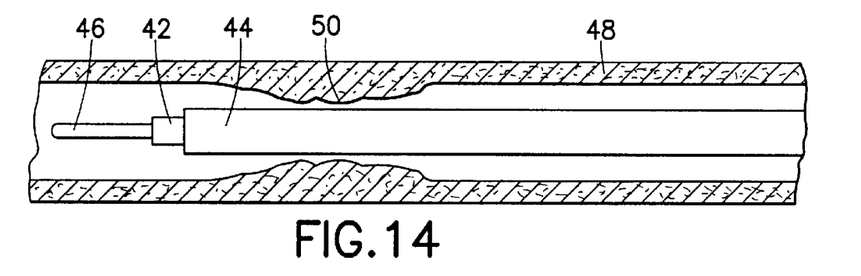
FIGS. 14 through 17 illustrate implantation of the first embodiment of the stent according to the invention.
Figure 15:
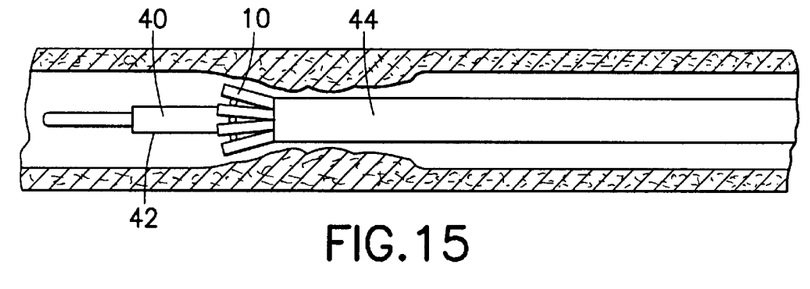
Figure 16:
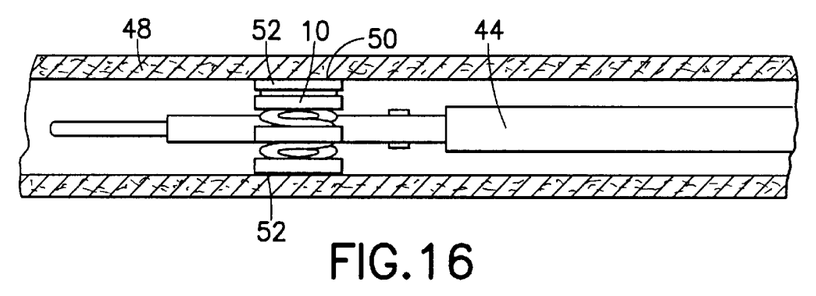
Figure 17:
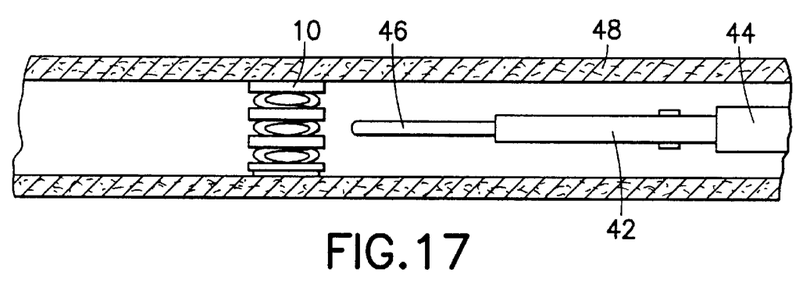

Regardless of the various above described arrangements of the self-expanding first embodiment of the stent of the invention, the stent may be deployed as follows. Turning to FIG. 13, the stent 10 is positioned at the distal end 40 of a catheter 42 with a lubricous sleeve 44 placed over the stent to hold the stent in a contracted state; i.e., with a relatively small diameter. Referring now to FIGS. 14 through 17, the stent 10 on the catheter 42 may then be moved to the lesion 50 in the blood vessel 48 by advancing the catheter over a guidewire 46 to the location of the lesion 50 (FIG. 14). Alternatively, the stent may be provided directly on the distal end of a guidewire, with a sleeve thereover, and advanced to the lesion site. The sleeve 44 is then withdrawn to permit the stent 10 to automatically expand (FIG. 15). Once the sleeve 44 is completely removed from over the stent 10, the stent will automatically completely expand at the site of the lesion 50 (FIG. 16). The deployment apparatus, i.e., the catheter 42, sleeve 44, and guidewire 46, may then be removed from the patient (FIG. 17).

Figure 18:
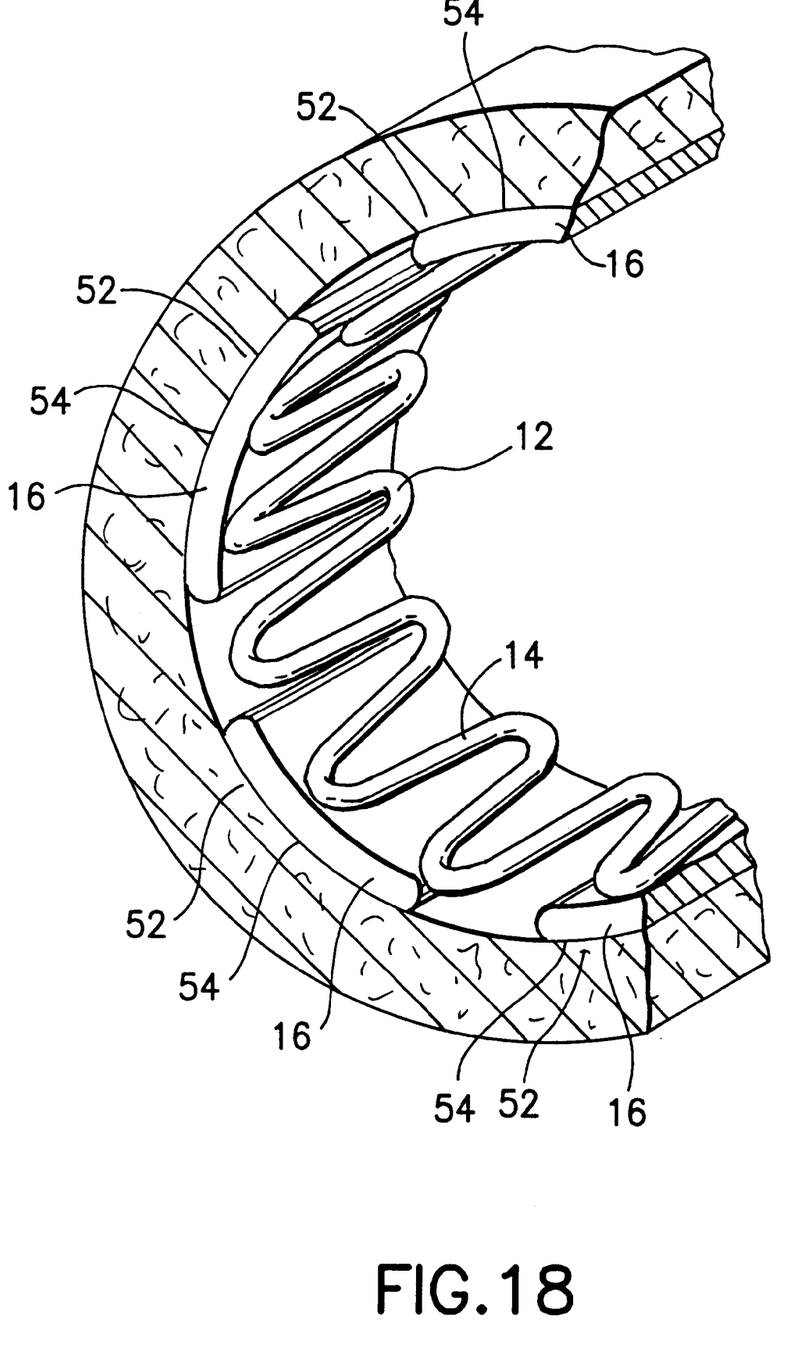
FIG. 18 is a greatly enlarged partial section perspective view of the first embodiment of the stent as implanted.

Turning now to FIG. 18, in situ, when the wire tubular form 14 of the stent 10 automatically expands, the foil members 16 move radially outward and exert pressure on the inner wall 52 of the blood vessel. The contact between the stent 10 and the wall 52 occurs at a relatively large contact surface 54, and therefore, irritation and trauma at the lesion 50 is minimized. In addition, especially with respect to relatively short stents, the tubular segments provide the stent with relatively superior strength.

The stent of the invention has several advantages. First, the foil members which contact the wall of the blood vessel provide both a relatively large surface area which conforms to the surface of the blood vessel. The flatness and relative size of the contact surface minimizes trauma to the implant location. Second, the spaced apart relation and arrangement of the foil members permits a relatively strong stent to be contracted into a size and structure which permits relatively easy advancement and deployment of the stent. Third, the foil members provide additional strength to the stent. Fourth, the foil members enhance fixation of the stent and further provide structural stability enabling the use of shorter, more maneuverable stents.

Figure 19:
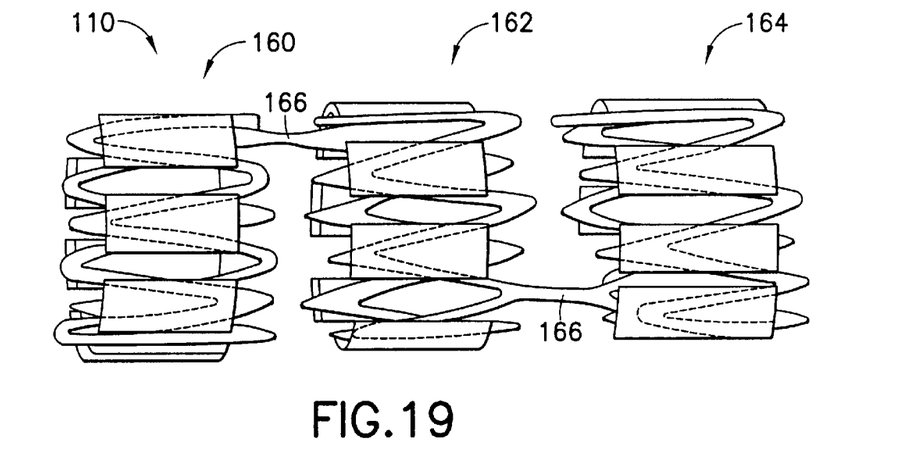
FIG. 19 is a stent comprising a segmented tubular form according to a second embodiment of the invention.

Referring now to FIG. 19, a second embodiment of the stent 110 of the invention, substantially similar to the first embodiment (with like parts having numbers incremented by 100) is shown. The stent 110 comprises a plurality of, e.g. three, self-expanding tubular segments 160, 162, 164 which are coupled together and a plurality of foil members 116 coupled to each tubular segment. Each of the tubular segments 160, 162, 164 is coupled to an adjacent segment by preferably a single link 166. Each link 166 is preferably resilient, e.g., of the same material as the wire 112 comprising each tubular segment 160, 162, 164, thereby permitting relatively longer stents in which the tubular segments 160, 162, 164 are bendable relative to each other. The stent of the second embodiment of the invention may be deployed by substantially the method as the stent of the first embodiment of the invention.

Figure 20:
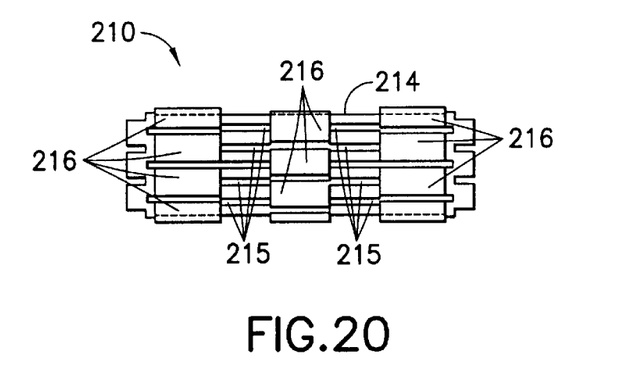
FIG. 20 is a side view of a third embodiment of the invention in a contracted state.
Figure 21:
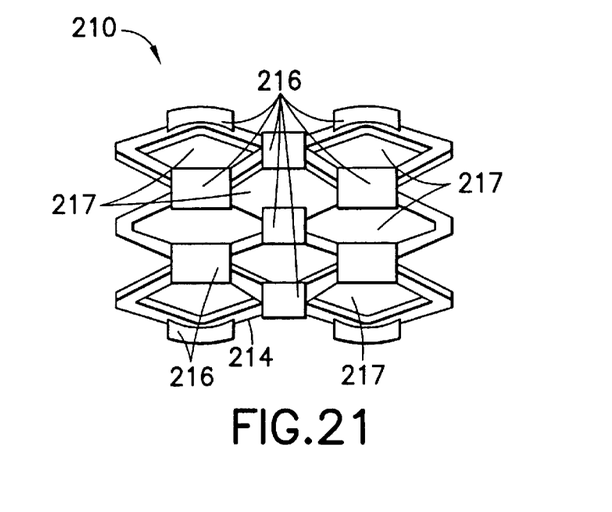
FIG. 21 is a side view of the third embodiment of the invention in an expanded state.

Turning now to FIGS. 20 and 21, a stent 210 according to a third embodiment of the invention is shown. The stent 210 is a pressure-expandable, e.g., balloon-expandable, stent comprised of a tube 214 having a plurality of slots 215 provided therein; i.e., the tube 214 is a 'slotted tube'. The tube 214 is preferably made from tantalum, stainless steel, platinum or another malleable biocompatible material. The slots 215 are preferably made by laser-cutting the tube material in a well-known manner. A plurality of foil members 216 are spaced about the outer periphery of the slotted tube 214. Preferably, the foil members 216 are arranged about a plurality of circumferential locations, each of the circumferential locations being longitudinally separated from each other on the outer periphery of the tube 214. The foil members 216 are coupled to the tube preferably by welding such that the welds (not shown) do not substantially impede the ability of the slotted tube 214 to be expanded in diameter. The stent, when contracted (FIG. 20), is provided with a relatively small diameter, e.g., capable of being advanced through arteries to the locus of a blood vessel lesion. When expanded (FIG. 21), the stent increases in diameter, moving the foil members radially outward and circumferentially spacing the foil members. In addition, when expanded, the slots 215 open to provide windows 217. Alternatively, rather than comprising a malleable slotted tube, the stent may comprise one or malleable wires provided in a tubular shape on which the plurality of foil members are provided. In addition, as described above with respect to the multisegment self-expanding stent, the pressure-expandable stent may also be provided in multi-segment form. The stent 210 preferably has the same range of lengths, and same preferred expanded and contracted diameters as the stent of the first embodiment of the invention.

Figure 22:
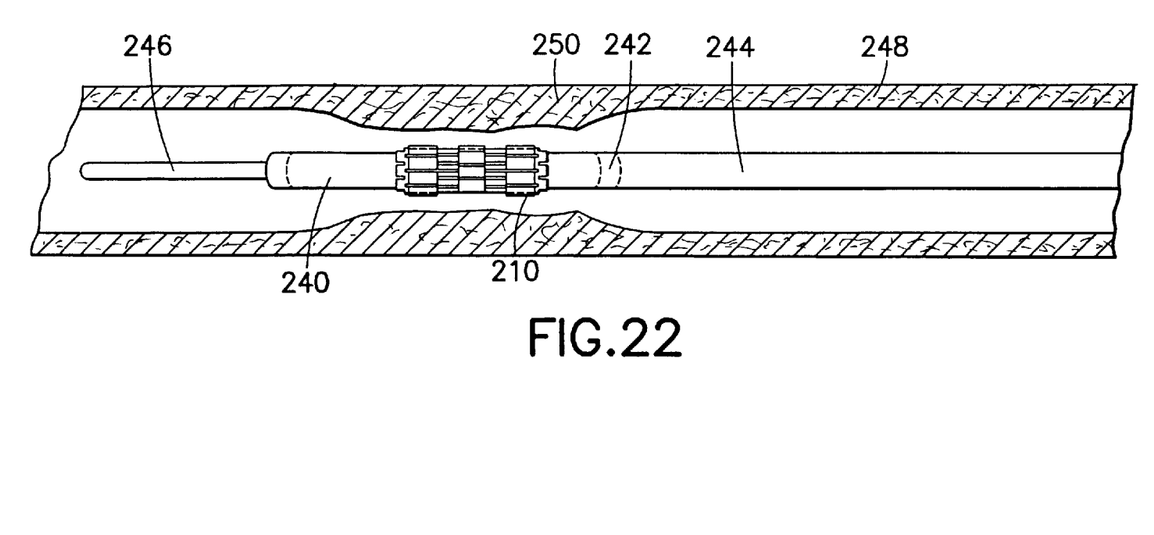
FIGS. 22 and 23 illustrate implantation of the third embodiment of the stent according to the invention.
Figure 23:
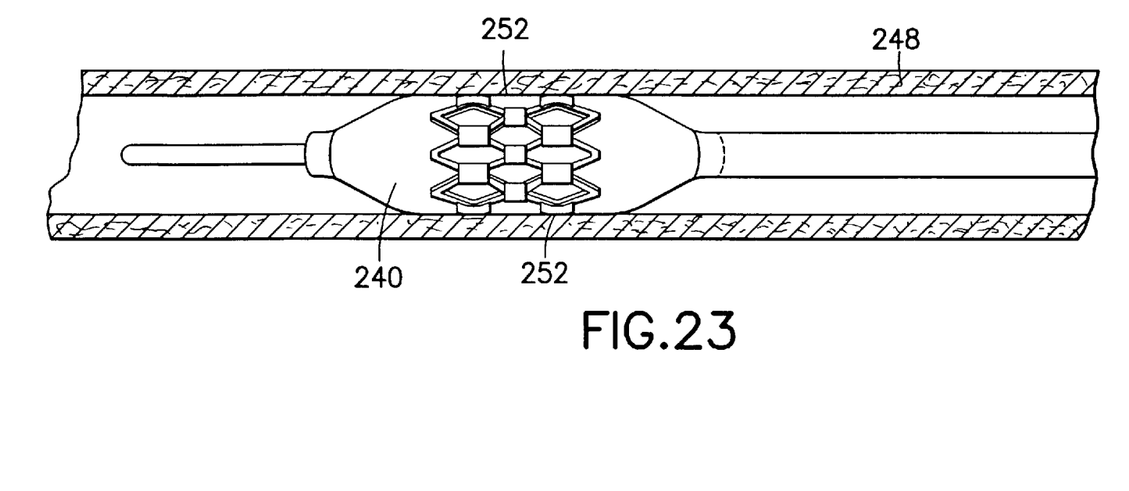

According to well-known methods for deployment of a pressure expandable stent, a stent 210 according to the invention is mounted on a balloon 240 at a distal end 242 of a balloon catheter 244 and advanced over a guidewire 246 through the blood vessel 248 to the site of the lesion 250 (FIG. 22). Once located at the lesion 250, the balloon 240 is expanded causing the malleable material of the stent 210 to expandably deform, and further causing the foil members 216 about the circumference of the stent to contact and support the inner wall 252 of the blood vessel 248. Similar advantage, as described above with respect to the self-expanding embodiment of the invention, is also provided to the pressure-expandable embodiment.

There have been described and illustrated herein several embodiments of an expandable stent. While particular embodiments of the invention have been described, it is not intended that the invention be limited thereto, as it is intended that the invention be as broad in scope as the art will allow and that the specification be read likewise. Thus, while the stent has been described as a vascular stent, and in particular a coronary stent, it will be appreciated that the stent design of the invention applies to other stents used elsewhere in the mammalian body. Therefore, while particular preferred dimensions have been disclosed with respect to the vascular stents, it will be appreciated that other dimensions may also be used. In addition, while particular materials for the tubular form and foil members of the stent have been disclosed, it will be appreciated that other materials may be used as well. Furthermore, while particular shapes of the bends for the self-expanding wire stent have been disclosed, it will be understood that other shapes may be used, and that more than one wire may also be used to create the tubular form. Also, while four to eight foil member are preferred around the circumference of the tubular form, it will be appreciated that fewer or more foil members may be used. Moreover, while the foil members have specifically been described with respect to the self-expanding embodiment as alternatively being perforate or mesh and as preferably having a coating or impregnation, it will be appreciated that the foil members of the pressure-expandable stent may likewise be constructed, coated, and/or impregnated. In addition, while the foil members are preferably welded to the underlying tubular form, the foil members may alternatively be coupled to the stent by other techniques, for example, soldering. Furthermore, while one or two welds have been disclosed, it will be appreciated that more than two welds may also be used. Moreover, while particular configurations of the foil members about the tubular form of the self-expanding and pressure-expandable stents have been disclosed, it will be appreciated that other configurations could be used as well. Also, while the terms "contracted" and "compressed" have been used to describe the stent as having the small diameter necessary for delivery to an implantation site, it will be appreciated that the terms, especially as applied to pressure expandable stents, should not be used to imply that the tube is under external pressure to provide the tube with a small diameter; i.e., a "contracted" or "compressed" pressure-expandable stent may be formed and naturally reside in the "contracted" or "compressed" state until internally pressurized to expand. Therefore, "contracted" and "compressed" are intended only to imply that the stent is in state having a small diameter relative to an expanded state. It will therefore be appreciated by those skilled in the art that yet other modifications could be made to the provided invention without deviating from its spirit and scope as so claimed.

What is claimed is:

1. An expandable endovascular support device, comprising:

a) a substantially tubular expandable form comprising at least one frame element having a first surface width, said tubular form having an outer periphery with a circumference, said tubular form movable from a contracted state in which said form has a first diameter to an expanded state in which said form has a second diameter greater than said first diameter; and b) a plurality of separate thin sheet foil members having second surface widths substantially greater than said first surface width, said foil members being substantially radially coupled about said circumference of said outer periphery, said foil members being provided in a first position when said expandable form is in said contracted state, wherein when said expandable form is in said expanded state, said foil member are moved radially apart from each other about said circumference relative to said first position.

2. An expandable endovascular support device according to claim 1, wherein:
   said foil members are curved.

3. An expandable endovascular support device according to claim 1, wherein:
   said foil members are comprised of one of stainless steel, titanium, platinum, and titanium-nickel alloy.

4. An expandable endovascular support device according to claim 1, wherein:
   said foil members are one of a perforate construct and a mesh construct.

5. An expandable endovascular support device according to claim 1, wherein:
   said foil members are at least one of coated and impregnated with at least one of PTFE, a thermoplastic elastomer, and heparin.

6. An expandable endovascular support device according to claim 1, wherein:
   said support device includes 4 to 8 foil members.

7. An expandable endovascular support device according to claim 1, wherein:
   said foil members have a thickness of approximately 0.003 inches to 0.006 inches.

8. An expandable endovascular support device according to claim 1, wherein:
   when said tubular form is in said contracted state, said foil members are oriented substantially tangential relative to said circumference.

9. An expandable endovascular support device according to claim 1, wherein:
   when said tubular form is in said contracted state, said foil members are oriented such that a first portion of each said foil member overlaps a second portion of an adjacent foil member.

10. An expandable endovascular support device according to claim 1, wherein:
    said foil members are arranged about a plurality of circumferences of said outer periphery, each of said circumferences being longitudinally separated from the other of said circumferences on said outer periphery of the said tubular form.

11. An expandable endovascular support device according to claim 1, wherein:
    said tubular form is self-expanding.

12. An expandable endovascular support device according to claim 11, wherein:
    said tubular form comprises at least one resilient wire.

13. An expandable endovascular support device according to claim 12, wherein:
    said at least one resilient wire is provided with a series of back and forth bends.

14. An expandable endovascular support device according to claim 1, wherein:
    said tubular form is pressure-expandable.

15. An expandable endovascular support device according to claim 14, wherein:
    said tubular form comprises one of a tube provided with a plurality of slots and a wire, said one of a tube and a wire being made from a malleable material.

16. An expandable endovascular support device according to claim 15, wherein:
    said malleable material comprises one of tantalum and stainless steel.

17. An expandable endovascular support device according to claim 1, comprising:
    a plurality of said substantially tubular expandable forms, each of said expandable forms being linked to another of said expandable forms such that said expandable forms are longitudinally aligned.

18. An expandable endovascular support device according to claim 17, wherein:
    each of said tubular expandable forms is provided with a plurality of said foil members.

19. An expandable endovascular support device according to claim 16, wherein:
    said foil members are coupled to said tubular expandable forms by at least one weld for each of said foil members.

20. An expandable support device for implantation within a mammalian body, said expandable support device, comprising:

a) a self-expanding tubular form comprising at least one frame element having a first surface width, said tubular form having an outer periphery with a circumference, said tubular form movable from a contracted state in which said form has a first diameter to an expanded state in which said form has a second diameter greater than said first diameter; and b) a plurality of separate thin sheet foil members having second surface widths substantially greater than said first surface width, said foil members being substantially radially coupled about said circumference of said outer periphery, said foil members being provided in a first position when said expandable tubular form is in said contracted state, wherein when said expandable form is in said expanded state, said foil member are moved radially apart from each other about said circumference relative to said first position.

21. An expandable support device according to claim 20, wherein:

when said tubular form is in said contracted state, said foil members are oriented substantially tangential relative to said circumference.

22. An expandable support device according to claim 20, wherein:

when said tubular form is in said contracted state, said foil members are oriented such that a first portion of each said foil member overlaps a second portion of an adjacent foil member.

23. An expandable support device according to claim 20, wherein:

said foil members are arranged about a plurality of circumferences of said outer periphery, each of said circumferences being longitudinally separated from the other of said circumferences on said outer periphery of the said tubular form.

24. An expandable support device according to claim 20, wherein:

said self-expanding tubular form includes at least one resilient wire a provided with a series of bends.

25. An expandable support device according to claim 20, wherein:

said foil members are one of a perforate construct and a mesh construct.

26. An expandable support device according to claim 20, wherein:

said foil members are at least one of coated and impregnated with at least one of PTFE, a thermoplastic elastomer, and heparin.

27. An expandable support device for implantation within a mammalian body, said expandable support device, comprising:

a) a pressure expandable tubular form comprising at least one frame element having a first surface width, said tubular form having an outer periphery with a circumference and an inner periphery, said tubular form movable from a contracted state in which said form has a first diameter to an expanded state in which said form has a second diameter greater than said first diameter; and b) a plurality of separate thin sheet foil members having second surface widths substantially greater than said first surface width, said foil members being substantially radially coupled about said circumference of said outer periphery, said foil members being provided in a first position when said expandable form is in said contracted state, wherein when said expandable form is in said expanded state, said foil member are moved radially apart from each other about said circumference relative to said first position.

28. An expandable support device according to claim 27, wherein:

said tubular form comprises a malleable material which can be moved from said contracted state to said expanded state by pressurizing said inner periphery of said expandable form.

29. An expandable support device according to claim 27, wherein:

when said tubular form is in said contracted state, said foil members are oriented substantially tangential relative to said circumference.

30. An expandable support device according to claim 27, wherein:

said foil members are arranged about a plurality of circumferences of said outer periphery, each of said circumferences being longitudinally separated from the other of said circumferences on said outer periphery of the said tubular form.

31. An expandable support device according to claim 27, wherein:

said foil members are one of a perforate construct and a mesh construct.

32. An expandable support device according to claim 27, wherein:

said foil members are at least one of coated and impregnated with at least one of PTFE, a thermoplastic elastomer, and heparin.

* * * * *